US00PP10593P

United States Patent [19]

Bergman

[11] Patent Number: Plant 10,593

[45] Date of Patent: Sep. 8, 1998

[54] HIBISCUS PLANT NAMED 'LIGHT WIND'

[75] Inventor: Wendy R. Bergman, Lehigh Acres, Fla.

[73] Assignee: Yoder Brothers, Inc., Barberton, Ohio

[21] Appl. No.: 806,711

[22] Filed: Feb. 27, 1997

[51] Int. Cl.[6] ..... A01H 5/00

[52] U.S. Cl. ..... Plt./67.8

[58] Field of Search ..... Plt./67.8

*Primary Examiner*—James R. Feyrer

*Attorney, Agent, or Firm*—C. A. Whealy

[57] ABSTRACT

A new and distinct cultivar of Hibiscus plant named 'Light Wind', characterized by its very dark leaves; long leaf petioles; upright and compact, uniform and symmetrical plant habit; very freely branching; freely flowering with numerous light pink-colored flowers with white throat color; long peduncles; good resistance to flower bud abscission; and excellent postproduction longevity.

2 Drawing Sheets

The present invention relates to a new and distinct cultivar of Hibiscus, botanically known as *Hibiscus rosa-sinensis*, and hereinafter referred to by the cultivar name Light Wind.

The new cultivar is a product of a planned breeding program conducted by the inventor in Alva, Fla. The objective of the breeding program is to create new Hibiscus cultivars having uniform plant habit, early flowering, numerous flowers per lateral branch, desirable flower color, resistance to flower bud abscission, and good postproduction longevity.

The new cultivar originated from a cross made by the inventor in Alva, Fla. of the proprietary seedling selection identified as number 1184 as the female, or seed, parent with the commerical cultivar Waikiki (disclosed in U.S. Plant Pat. No. 7,834) as the male, or pollen parent. Compared to plants of the dark orange-colored proprietary seedling selection number 1184, plants of the new Hibiscus have a more uniform plant habit, more flowers and are more freely branching. Compared to plants of the cultivar Waikiki, plants of the new Hibiscus have more upright growth habit, darker foliage, smaller flowers, lighter flower color, and more uniform flowering. In addition, plants of the new Hibiscus have a white flower throat color whereas plants of the cultivar Waikiki have a dark red flower throat color.

The cultivar Light Wind was discovered and selected by the inventor as a flowering plant within the progeny of the stated cross in a controlled environment in Alva, Fla., on Aug. 26, 1993. The selection of this plant was based on its desirable flower color, resistance to flower bud abscission, good postproduction longevity, and uniform plant habit and flowering.

The new Hibiscus is similar to plants of the nonpatented cultivar Pink Versicolor. In side-by-side comparisons conducted in Alva, Fla., plants of the new cultivar differ from plants of the cultivar Pink Versicolor in the following characteristics:

1. Plants of the new Hibiscus have smaller leaves than plants of the cultivar Pink Versicolor.
2. Plants of the new Hibiscus have more flowers than plants of the cultivar Pink Versicolor.
3. Plants of the new Hibiscus have lighter pink-colored flowers than plants of the cultivar Pink Versicolor.
4. Flower throat color of plants of the new Hibsicus is white whereas flower throat color of plants of the cultivar Pink Versicolor is dark red.
5. Plants of the new Hibiscus flower are more resistant to flower bud abscission than plants of the cultivar Pink Versicolor.

Asexual reproduction of the new cultivar by terminal cuttings taken in a controlled environment in Alva, Fla., has shown that the unique features of this new Hibiscus are stable and reproduced true to type in successive generations.

The cultivar Light Wind has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'Light Wind'. These characteristics in combination distinguish 'Light Wind' as a new and distinct cultivar:

1. Very dark green leaves with long petioles.
2. Upright and compact, uniform and symmetrical plant habit.
3. Very freely branching.
4. Freely flowering, numerous light pink-colored flowers with white throat color.
5. Good resistance to flower bud abscission.
6. Excellent postproduction longevity.

The accompanying colored photographs illustrate the overall appearance of the new cultivar, showing the colors as true as it is reasonably possible to obtain in colored reproductions of this type.

The first photograph comprises a side perspective view of typical plant of 'Light Wind'. The second photograph comprises a close-up view of a typical flower of 'Light Wind'. Flower and foliage colors in the photographs may appear different from the actual colors due to the light reflectance.

The aformentioned and following observations, measurements, values, and comparisons describe plants grown in Alva, Fla., in 15-cm containers with day temperatures ranging from 16° to 35° C. and night temperatures ranging from 10° to 24° C. Plants were grown under a polypropylene covering with light levels ranging from 6,000 to 9,000 footcandles.

In the following descriptions, color references are made to The Royal Horticultural Society Colour Chart except where general terms of ordinary dictionary significance are used.

Botanical classification: *Hibiscus rosa-sinensis* cv. Light Wind.

Parentage:

*Male or pollen parent.*—*Hibiscus rosa-sinensis* cv. Waikiki (U.S. Plant Pat. No. 7,834).

*Female or seed parent.*—Proprietary seedling selection of *Hibiscus rosa-sinensis* identified as number 1184.

Propagation:

*Type.*—By terminal cuttings.

*Time to develop roots.*—About 28 days at temperatures of 24° C.

*Rooting habit.*—Moderately vigorous, thick and well-branched.

Plant description:

*Plant form and growth habit.*—Perennial, evergreen, upright and compact, inverted triangle, uniform and symmetrical plant habit. Moderate vigor.

*Branching habit.*—Very freely branching, usually five lateral branches develop after removal of terminal apex.

*Plant height, soil level to top of flowers.*—About 26 cm.

*Plant diameter, area of spread.*—About 33 cm.

*Lateral branch description.*—Length: About 8 cm. Diameter: About 5 mm. Color: Immature: 200B with green tones. Mature: 200A.

Foliage description:

*Arrangement.*—Alternate, single.

*Leaf size, largest leaves.*—Length: About 9 cm. Width: About 6 cm.

*Leaf shape.*—Ovate.

*Leaf apex.*—Pointed.

*Leaf base.*—Obtuse.

*Margin type.*—Dentate.

*Texture.*—Glabrous and glossy on both surfaces.

*Aspect.*—Slightly undulating.

*Color.*—Young foliage, upper surface: 147A. Young foliage, lower surface: 146A. Mature foliage, upper surface: Very dark green, greener than 147A. Mature foliage, lower surface: 147A. Venation, upper surface: Darker than 147A. Venation, lower surface: 147A.

*Petiole.*—Length: About 4.5 cm. Diameter: About 2 mm. Texture: Pubescence on upper surface. Color: 200A/200B with green overtones.

Flower description:

*Natural flowering season.*—Usually spring and summer or during periods of warm weather.

*Flower arrangements.*—Flowers arranged singly at terminal leaf axils. Freely flowering with usually four to six flower buds and/or open flowers per terminal apex. Flowers face upright and outward.

*Flower appearance.*—Star-shaped single. Light pink-colored petals with white throat color. Flowers are open for about one day before closing. Flowers persistent.

*Flower diameter.*—About 14 cm.

*Flower bud (just before opening).*—Rate of opening: About one day depending on temperatures. Length: About 5 cm. Diameter: About 1.3 cm. Shape: Columnar. Color: Light pink with green, 146A, overtones.

*Petals.*—Texture: Satiny, smooth. Arrangements: Corolla consists of five petals that overlap. Shape: Narrowly spatulate with rounded apex. Margin: Entire, undulating. Size: Length: About 7.5 cm. Width: About 4 cm. Color: Upper surface: Light pink, 55D, at margin, darker pink, 52D, at center with white at base. Veins are dark pink, 55A. Lower surface: Very light pink with yellow, 22D, where petals overlap. Throat: White, 155D.

*Sepals.*—Appearance: Six sepals fused into a star-shaped calyx. Shape: Linear. Texture: Smooth. Color, outer surface: 146A.

*Peduncles.*—Length: About 2 cm. Diameter: About 3.5 mm. Angle: Upright. Strength: Strong, rigid. Color: 200B.

*Reproductive organs.*—Androecium: Stamen number: Numerous. Stamen length: About 6 mm. Anther shape: Globular. Anther size: About 1 mm. Amount of pollen: Abundant. Pollen color: 21A. Gynoecium: Pistil length: About 10 cm. Style length: About 8.5 cm. Style color: 11D. Stigma shape: Round. Stigma diameter: About 2.5 mm. Stigma color: 21A. Ovary color: White.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Light Wind', as illustrated and described.

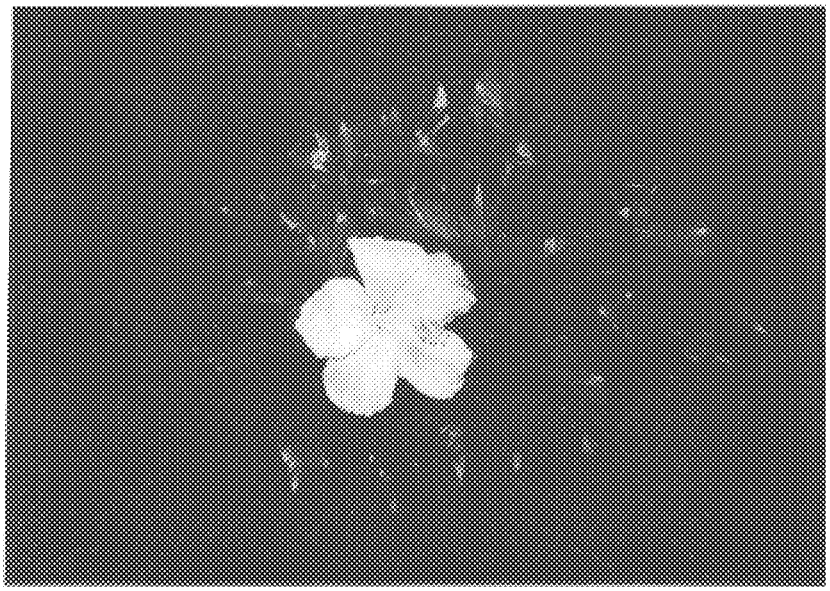

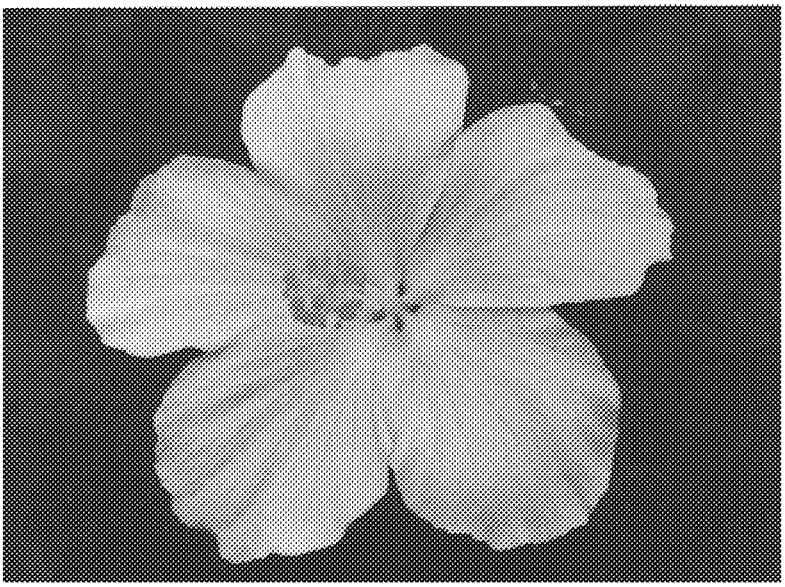

* * * * *